United States Patent
Klatzmann et al.

(10) Patent No.: US 11,534,479 B2
(45) Date of Patent: Dec. 27, 2022

(54) USE OF INTERLEUKIN 2 FOR TREATING SJÖGREN'S SYNDROME

(71) Applicants: ILTOO PHARMA, Paris (FR); ASSISTANCE PUBLIQUE—HÔPITAUX DE PARIS, Paris (FR); SORBONNE UNIVERSITÉ, Paris (FR)

(72) Inventors: David Klatzmann, Paris (FR); Roberta Lorenzon, Paris (FR); Michèle Rosenzwajg, Paris (FR); Patrice Cacoub, Le Perreux (FR); Arsene Mekinian, Paris (FR)

(73) Assignees: ILTOO PHARMA, Paris (FR); ASSISTANCE PUBLIQUE—HÔPITAUX DE PARIS, Paris (FR); SORBONNE UNIVERSITÉ, Paris (FR)

( * ) Notice: Subject to any disclaimer, the term of this patent is extended or adjusted under 35 U.S.C. 154(b) by 169 days.

(21) Appl. No.: 16/965,700

(22) PCT Filed: Feb. 18, 2019

(86) PCT No.: PCT/EP2019/054002
§ 371 (c)(1),
(2) Date: Jul. 29, 2020

(87) PCT Pub. No.: WO2019/158764
PCT Pub. Date: Aug. 22, 2019

(65) Prior Publication Data
US 2021/0121532 A1    Apr. 29, 2021

(30) Foreign Application Priority Data

Feb. 16, 2018  (EP) .................................... 18305170

(51) Int. Cl.
| | | |
|---|---|---|
| *A61K 38/20* | (2006.01) | |
| *A61K 47/68* | (2017.01) | |
| *A61K 47/60* | (2017.01) | |
| *A61P 37/00* | (2006.01) | |

(52) U.S. Cl.
CPC .......... *A61K 38/2013* (2013.01); *A61K 47/60* (2017.08); *A61K 47/68* (2017.08); *A61P 37/00* (2018.01)

(58) Field of Classification Search
CPC .................................................. A61K 38/2013
See application file for complete search history.

(56) References Cited

FOREIGN PATENT DOCUMENTS

| CN | 104189892 A | 12/2014 |
|---|---|---|
| WO | WO 2012/123381 A1 | 9/2012 |
| WO | WO 2017/042370 A1 | 3/2017 |

*Primary Examiner* — Prema M Mertz
(74) *Attorney, Agent, or Firm* — McDermott Will & Emery LLP

(57) ABSTRACT

The invention relates to the use of interleukin-2 in treating Sjögren's syndrome in a subject, wherein IL-2 is to be administered at a low dose of less than about 3.5 MIU/day.

14 Claims, 2 Drawing Sheets

Specification includes a Sequence Listing.

USE OF INTERLEUKIN 2 FOR TREATING SJÖGREN'S SYNDROME

RELATED APPLICATIONS

This application is a national stage filing under 35 U.S.C. § 371 of international application number PCT/EP2019/054002, filed on Feb. 18, 2019, which claims the benefit of priority to European Patent Application No. 18305170.5, filed on Feb. 16, 2018. The entire contents of each of the prior applications are herein incorporated by reference.

SEQUENCE LISTING

The instant application contains a Sequence Listing, which has been filed electronically in ASCII format and is hereby incorporated by reference in its entirety. Said ASCII copy, created on Dec. 28, 2020, is named 112360-0024-70023US00_SUBSEQ.txt and is 3,000 bytes in size.

BACKGROUND OF THE INVENTION

Primary Sjögren's syndrome (pSS) is a mild indolent chronic disease mainly characterized by mucosal dryness in the majority of cases. A subgroup of patients displays extra-glandular manifestations. Virtually any organs and systems can be affected, leading to serious disease prognosis. Pain and stiffness in the joints with mild swelling may occur in some patients, even in those without associated rheumatoid arthritis or lupus. Rashes on the arms and legs related to inflammation in small blood vessels and inflammation in the lungs, liver, and kidney may occur rarely. Numbness, tingling, and weakness also have been described in some patients. The parotid gland can become swollen and inflamed in some patients.

No effective cure is available. Treatment is typically designed to lessen the most bothersome symptoms. Dry eyes usually respond to artificial tears applied regularly during the day or to gels applied at night. Hydroxychloroquine, an antimalarial drug, may be helpful in some patients with Sjögren's syndrome by reducing joint pain and rash. Patients with rare but serious systemic symptoms, such as fever, rashes, abdominal pain, or lung or kidney problems, may require treatment with corticosteroids such as prednisone and/or immunosuppressive agents like methotrexate, azathioprine, mycophenolate or cyclophosphamide. In addition, rituximab and other biological therapies that target Th17 cytokines, cytokine receptors and transcription factors are being proposed.

However there is a clear need for more effective and safer drug in managing Sjögren's syndrome.

SUMMARY OF THE INVENTION

It is herein provided a method for treating Sjögren's syndrome in a subject by administration of a low dose of IL-2, namely a dose of at most 3.5 MIU/day.

More specifically the invention provides IL-2 for use in treating Sjögren's syndrome in a subject, wherein IL-2 is to be administered at a dose of about 1 to about 2 MIU/day, wherein the treatment comprises at least a first course wherein interleukin-2 is administered once per day during at least 2 or 3 consecutive days, preferably during 3 to 7, still preferably during 4 to 5 consecutive days, preferably followed by a maintenance dose after about six days or one week to about 4 weeks.

This dosage has been chosen to effectively expand and activate Tregs without substantially activating Teffs. The consequence is a dramatic increase in the Treg/Teff balance in the subject, without impact on its immunocompetency.

LEGENDS TO THE FIGURES

DETAILED DESCRIPTION OF THE INVENTION

Definitions

Figure 1:
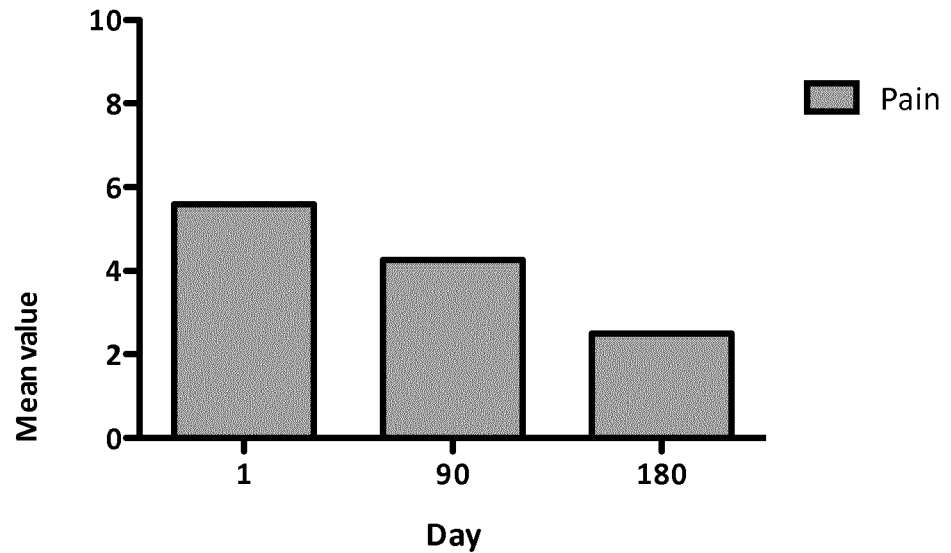
FIG. 1 is a graph that shows alleviation of pain (arthralgia) in 7 subjects with Sjögren's syndrome.

The "subject" or "patient" to be treated may be any mammal, preferably a human being. The human subject may be a child, an adult or an elder. Sjögren's syndrome is more frequent in women, but any gender is encompassed. Typically the patient may especially be an adult who is more than 40 years old, or more than 50 or 60 years old. In other embodiments, the subject is a non-human mammal, such as a dog. A subset of patients with extraglandular involvement, vasculitis, hypocomplementaemia and/or cryoglobulinaemia is particularly encompassed. The patients include patients affected with a "Primary Sjögren's syndrome", namely with no other rheumatic disease, and patients affected with a "Secondary Sjögren's syndrome", namely patients who have another rheumatologic disease, typically systemic lupus erythematosus or rheumatoid arthritis.

The term "treating" or "treatment" means any improvement in the disease. It includes alleviating at least one symptom, or reducing the severity or the development of the disease. In particular it includes reducing the risk, occurrence or severity of acute episodes (flares).

The term "treating" or "treatment" encompasses reducing the progression of the disease. In particular the invention encompasses preventing or slowing down the progression of Sjögren's syndrome. The term "treating" or "treatment" further encompasses prophylactic treatment, by reducing the risk or delaying the onset of the disease, especially in a subject who is asymptomatic but has been diagnosed as being "at risk".

The risk factors that predispose a person to Sjögren's syndrome include subjects with a family history of Sjögren's syndrome or of any autoimmune disease.

"Regulatory T cells" or "Tregs" are T lymphocytes having immunosuppressive activity. Natural Tregs are characterized as CD4+CD25+Foxp3+ cells. Tregs play a major role in the control of inflammatory diseases, although their mode of action in such disease is not well understood. In fact, in most inflammatory diseases, Treg depletion exacerbates disease while Treg addition decreases it. Most Tregs are CD4+ cells, although there also exists a rare population of CD8+Foxp3+ T lymphocytes with a suppressive activity.

Within the context of this application, "effector T cells" (or "Teff") designates conventional T lymphocytes other than Tregs (sometimes also referred to as Tconv in the literature), which express one or more T cell receptor (TCR)

and perform effector functions (e.g., cytotoxic activity, cytokine secretion, anti-self recognition, etc). Major populations of human Teff according to this invention include CD4+ T helper lymphocytes (e.g., Th0, Th1, Th17) and CD4+ or CD8+ cytotoxic T lymphocytes, and they can be specific for self or non-self antigens.

Sjögren's Syndrome

The present invention relates to administering interleukin 2 (IL-2) for use in treating Sjögren's syndrome.

More specifically, the present invention relates to alleviating articular and extra-articular symptoms, more particularly glandular symptoms or fatigue in patients with Sjögren's syndrome. In particular, the invention alleviates pain in the subject.

In a particular aspect, it is provided a method for treating articular symptoms of Sjögren's syndrome (such as arthralgia or morning stiffness) in a patient in need thereof. In a particular embodiment the present invention aims at preventing or alleviating articular symptoms in patients with Sjögren's syndrome, such as arthralgia or morning stiffness.

Interleukin 2 (IL-2)

As used herein, Interleukin-2 (IL-2) encompasses mammal wild type Interleukin-2, and variants thereof. Preferably, IL-2 is a human IL-2, or a variant thereof.

Active variants of IL-2 have been disclosed in the literature. Variants of the native IL-2 can be fragments, analogues, and derivatives thereof. By "fragment" is intended a polypeptide comprising only a part of the polypeptide sequence. An "analogue" designates a polypeptide comprising the native polypeptide sequence with one or more amino acid substitutions, insertions, or deletions. Muteins and pseudopeptides are specific examples of analogues. "Derivatives" include any modified native IL-2 polypeptide or fragment or analogue thereof, such as glycosylated, phosphorylated, fused to another polypeptide or molecule, polymerized, etc., or through chemical or enzymatic modification or addition to improve the properties of IL-2 (e.g., stability, specificity, etc.). The IL-2 moiety of active variants generally has at least 75%, preferably at least 80%, 85%, more preferably at least 90% or at least 95% amino acid sequence identity to the amino acid sequence of the reference IL-2 polypeptide, for instance mature wild type human IL-2.

Methods for determining whether a variant IL-2 polypeptide is active are available in the art. An active variant is defined as a variant that shows an ability to stimulate Tregs, including variants with an improved ability, or a similar ability, or even a reduced ability to stimulate Tregs when compared to wild-type IL-2 or aldesleukin (as defined below), to the extent it does not stimulate Teffs more than it stimulates Tregs at the dosage herein defined. Methods for testing whether a candidate molecule stimulate T cells, and Tregs in particular, are well-known. Variants may be tested for their ability to stimulate effector T cells (such as CD4+ Foxp3− or CD8+ T cells), NK cells or CD4+Foxp3+ Tregs.

Monitoring STAT5 phosphorylation is a simple way of assessing variants for their ability to preferentially stimulate Tregs, as described in Yu et al, Diabetes 2015; 64:2172-2183. A variant is particularly useful when a given level of STAT5 phosphorylation is achieved with doses at least 10 times inferior in Tregs than in other cells, including Teffs.

In another example, before analyzing, total PBMC are activated (e.g. at 4×10$^6$ cells per well) with anti-CD3 antibody (e.g. at 100 ng/ml), and cultured. On day 3 of culture, cells are typically washed and rested in fresh media for 3 days. Cells are then washed and contacted with IL-2 variants (e.g. at either 10 nM or 100 pM). About three days later, cells are counted and analyzed by flow cytometry.

Another in vitro method for determining the ability of a candidate variant to preferentially stimulate Treg cells is the measure of gene expression, as also described in Yu et al, supra.

Said active variants induce signaling events that preferentially induce survival, proliferation, activation and/or function of Treg cells. In certain embodiments, the IL-2 variant retains the capacity to stimulate, in Treg cells, STAT5 phosphorylation and/or phosphorylation of one or more of signaling molecules downstream of the IL-2R, e.g., p38, ERK, SYK and LCK. In other embodiments, the IL-2 variant retains the capacity to stimulate, in Treg cells, transcription or protein expression of genes or proteins, such as FOXP3 or IL-10, that are important for Treg cell survival, proliferation, activation and/or function. In other embodiments, the IL-2 variant exhibits a reduced capacity to stimulate endocytosis of IL-2/IL-2R complexes on the surface of CD25+ T cells. In other embodiments, the IL-2 variant demonstrates inefficient, reduced, or absence of stimulation of PI3-kinase signaling, such as inefficient, reduced or absent phosphorylation of AKT and/or mTOR (mammalian target of rapamycin). In yet other embodiments, the IL-2 variant retains the ability of wild type IL-2 to stimulate STAT5 phosphorylation and/or phosphorylation of one or more of signaling molecules downstream of the IL-2R in Treg cells, yet demonstrates inefficient, reduced, or absent phosphorylation of STAT5, AKT and/or mTOR or other signaling molecules downstream of the IL-2R in FOXP3−CD4+ or CD8+ T cells or NK cells. In other embodiments, the IL-2 variant is inefficient or incapable of stimulating survival, growth, activation and/or function of FOXP3−CD4+ or CD8+ T cells or NK cells.

In all cases, these variants have the capacity to stimulate cell lines such as CTLL-2 or HT-2 which can be universally used to determined their biological activity.

As used herein, "wild type IL-2" means IL-2, whether native or recombinant, having the 133 normally occurring amino acid sequence of native human IL-2 (SEQ ID NO: 1, which is the IL-2 sequence less the signal peptide, consisting of an additional 20 N-terminal amino acids), whose amino acid sequence is described in Fujita, et. al., PNAS USA, 80, 7437-7441 (1983).

As used herein, "IL-2 mutein" means a polypeptide in which specific substitutions to the human mature interleukin-2 protein have been made.

Examples of IL-2 variants are disclosed, for instance, in EP109748, EP136489, U.S. Pat. No. 4,752,585; EP200280, EP118617, WO99/60128, EP2288372, U.S. Pat. Nos. 9,616, 105, 9,580,486, WO2010/085495, WO2016/164937.

For instance, certain mutations may result in a reduced affinity for the signaling chains of the IL-2 receptor (IL-2Rβ/CD122 and/or IL-2Rγ/CD132) and/or a reduced capacity to induce a signaling event from one or both subunits of the IL-2 receptor. Other mutations may confer higher affinity for CD25 (IL-2Rα).

Particular examples of useful variants include IL-2 muteins which show at least one amino acid substitution at position D20, N30, Y31, K35, V69, Q74, N88, V91, or Q126, numbered in accordance with wild type IL-2, meaning that the chosen amino acid is identified with reference to the position at which that amino acid normally occurs in the mature sequence of wild type IL-2 of SEQ ID NO:1.

Preferred IL-2 muteins comprise at least one substitution at position D20H, D20I, D20Y, N30S, Y31H, K35R, V69AP, Q74, N88R, N88D, N88G, N88I, V91K, or Q126L We prefer conservative modifications and substitutions at other positions of IL-2 (i. e., those that have a minimal effect on the secondary or tertiary structure of the mutein).

Such conservative substitutions include those described by Dayhoff in The Atlas of Protein Sequence and Structure 5 (1978), and by Argos in EMBO J., 8: 779-785 (1989).

For example, amino acids belonging to one of the following groups represent conservative changes: -ala, pro, gly, gln, asn, ser, thr; -cys, ser, tyr, thr; -val, ile, leu, met, ala, phe; -lys, arg, his; -phe, tyr, trp, his; and -asp, glu.

Variants with mutations which disrupt the binding to the α subunit of IL-2R are not preferred, as those mutants may have a reduced capacity to stimulate Tregs.

IL-2 can be produced by DNA recombinant technique. The host organism used to express a recombinant DNA encoding IL-2 may be prokaryotic (a bacterium such as *E. coli*) or eukaryotic (e.g., a yeast, fungus, plant or mammalian cell). Processes for producing IL-2 have been described e.g., in U.S. Pat. Nos. 4,656,132; 4,748,234; 4,530,787; or 4,748,234, incorporated therein by reference.

Alternatively, IL-2 can be produced by chemical peptide synthesis. For instance, IL-2 can be produced by the parallel synthesis of shorter peptides that are subsequently assembled to yield the complete sequence of IL-2 with the correct disulfide bridge. A synthesis of Interleukin-2 is illustrated for instance in Asahina et al., Angewandte Chemie International Edition, 2015, Vol. 54, Issue 28, 8226-8230, the disclosure of which being incorporated by reference herein. In some embodiment, IL-2 is a variant having at least 80%, preferably at least 90%, 95%, 98%, 99%, sequence identity with a mature wildtype human IL-2. The variant can be glycosylated or non-glycosylated.

IL-2 is commercially available, including for pharmaceutical uses, and it is authorized for use in human patients. Suitable commercial forms include, e.g.

Proleukin® (aldesleukin) is a recombinant unglycosylated des-alanyl-1, serine-125 human interleukin-2, produced in *E.coli*.

Roncoleukin® is a recombinant human IL-2 produced in yeast.

In a preferred embodiment, IL-2 is aldesleukin. Aldesleukin is the active ingredient of Proleukin® Aldesleukin is an unglycosylated variant of mature human IL-2 comprising two amino acid modifications as compared to the sequence of mature human IL-2: the deletion of the first amino acid (alanine) and the substitution of cysteine at position 125 by serine.

The amino acid sequence of aldesleukin is provided as SEQ ID NO:2.

IL-2 for use in the present invention is preferably in essentially pure form, e.g., at a purity of 95% or more, further preferably 96, 97, 98 or 99% pure.

The biological activity of IL-2 is typically determined in a standard cell proliferation assay using an IL-2 dependent cell line, such as CTLL-2 or HT-2.

For instance, the biological activity of IL-2 may be determined by a cell-based assay performed on HT-2 cell line (clone A5E, ATCC® CRL-1841™) whose growth is dependent on IL-2. Cell growth in the presence of a range of test interleukin-2 product is compared with the growth recorded with IL-2 international standard (WHO 2nd International Standard for INTERLEUKIN 2 (Human, rDNA derived) NIBSC code: 86/500). Cell growth is measured after addition and transformation of [3-(4,5-dimethylthiazol-2-yl)-5-(3-carboxymethoxyphenyl)-2-(4-sulfophenyl)-2H-tetrazolium (inner salt, MTS) into formazan by active viable cells. Formazan concentration is then measured by spectrophotometry at 490 nm.

In a preferred embodiment, IL-2 as used in the present invention is des-alanyl-1, serine-125 human interleukin-2, preferably produced recombinantly. In a particular embodiment it is unglycosylated, preferably it is produced in *E.coli*.

The IL-2 may be used alone or in combination with any other therapeutically active agent. In a particular embodiment, the IL-2 is conjugated to a water-soluble polymer, such as polyethylene glycol (PEG). A preferred conjugate is described in patent application WO2012/065086, wherein the conjugate comprises a water-soluble polymer such as PEG covalently attached via a releasable linkage to an amine group of an IL-2 moeity.

In a particular embodiment, the IL-2 may be mutated at position D109C (with the C residue being capable of binding a PEG moiety), as described e.g. in international patent application WO2016/0025385.

In another particular embodiment, the IL-2 is fused to an immunoglobulin, preferably an IgG, preferably a human IgG, or preferably to a Fc region of an immunoglobulin. On may also use a particular fusion construct, that comprises two IL-2 proteins fused to one immunoglobulin, is disclosed e.g. in WO2014/023752 and WO2015/118016.

In another embodiment, the IL-2 is fused at the N-terminal end of a Fc moiety, either directly or preferably through a peptide linker, e.g. an 8 to 12 amino acid linker, as described e.g. in international patent application WO2016/014428.

Dosage and Regimen

The standard measure of an amount IL-2 is the International Unit (IU), which technically is not a fixed weight of protein but the amount that produces a fixed biological effect in a specific cell proliferation assay, as determined by the World Health Organization (WHO). The reason is that i) the weight varies depending on the exact sequence of the molecule and its glycosylation profile, and ii) what matters is the activity, not the weight of the molecule.

The principle of the International Unit is precisely to provide a standard to which any IL-2 molecule can be compared (regardless of their source, or their sequence, including wild-type or active variant sequences).

In practice, the WHO provide ampoules containing an IL-2 molecule that has been calibrated and serves as the reference to determine the dosage of a given preparation of IL-2 (again regardless of the source or sequence of said IL-2) defined by its potency. For instance, to determine the dosage of a given preparation of IL-2, the biological activity of the candidate IL-2 preparation is measured in a standard cell proliferation assay using an IL-2 dependent cell line, such as CTLL-2, and compared with the biological activity of the standard. The cells are grown in the presence of different doses of the standard. A dose-response effect of IL-2 is established, where the concentration of IL-2 is plotted on the X axis as IU and the measure of proliferation (pr) is on the Y axis. When one wants to determine the activity of any IL-2 product of unknown activity, the product is used to grow the IL-2 dependent cells and the proliferation is measured. The pr value is then plotted on the Y axis and from that value a line parallel to the X axis is drawn. From the point of intersection of this line with the dose response line, a line parallel to the Y axis is then drawn. Its intersection with the X axis provides the activity of the candidate IL-2 product in IU.

Any change of the WHO standard ampoules do not impact the International Unit nor the determination of a dosage of any IL-2 preparation.

The 1st standard (WHO international Standard coded 86/504, dated 1987) contained a purified glycosylated IL-2 derived from Jurkat cells and was arbitrarily assigned a potency of 100 IU/ampoule. As the stocks of the 1st international standard (IS) were running low, the WHO had to replace it. The WHO provided another calibrated IL-2 ampoule, this time produced using E. coli. The 2nd standard ampoules contained 210 IU of biological activity per ampoule. The change of standard ampoules does not mean that the IU changes. So, determining the dosage of a test IL-2 preparation will not vary whether one uses the 1st standard ampoule or the 2nd standard ampoule, or a subsequent standard ampoule, as a reference.

According to the invention, IL-2 is preferably administered at a dosage ranging from about 1 MIU/day to about 2 MIU/day. This dosage is particularly suitable for human subjects.

This dosage effectively activates Tregs without substantially activating Teffs. The consequence is a dramatic increase in the Treg/Teff balance in the subject. At this dosage, IL-2 substantially avoids side effects, while very substantially inducing Tregs.

In a preferred embodiment, particularly advantageous for subcutaneous administration, IL-2 is administered at a dose of 1, 1.5 or 2 MIU/day.

According to the invention, the treatment typically comprises at least a first course wherein interleukin-2 is administered once per day during at least about 2 or 3 consecutive days, preferably during 3 to 7, still preferably during 4 to 5 consecutive days, preferably followed by a maintenance dose after about six days or about 1 to about 4 weeks. Such induction course may be repeated, e.g. twice or three times, before the maintenance course starts.

The maintenance dose is typically administered during at least one month, preferably at least about 3 months, still preferably at least about 6 months. In a preferred embodiment, the maintenance dose is administered between about 3 months and about 12 months, preferably between about 6 months and about 12 months.

The maintenance period may be repeated.

In a preferred embodiment, the maintenance treatment consists of an administration of interleukin-2 once or twice a week, or every one or two weeks.

In a preferred embodiment, the maintenance treatment consists of an administration of interleukin-2 once or twice a week, every one or two weeks, during a period of at least one month, preferably from about 3 months to about 12 months.

Preferably the maintenance dosage is substantially the same as the first course dosage, or it can be a lower or higher dosage.

In a preferred embodiment, the treatment comprises at least a first course wherein interleukin-2 is administered at a dosage of at most 3.5 MIU/day, preferably about 1 to about 2 MIU/day, preferably 1-1.5 MIU/day, once per day during 2 or 3 to 7 days, preferably 5 days, followed by a maintenance dose after one to two weeks, of about 1 to about 2 MIU/day, preferably 1-1.5 MIU/day every 2 weeks, during at least three months, preferably at least six months.

In another embodiment, especially when the IL-2 molecule is a variant with longer half-life and/or is conjugated to a moiety that improves the half-life of the conjugate, the regimen is adjusted to the extent the Treg increase during maintenance remains at least 1.3, 1.5, 1.7, 1.9, or at least twice the baseline Treg level. For that purpose, in an embodiment, the regimen may be defined as a first (induction) course consisting of a dosage of at most 3.5 MIU one per day during 1 to 3 days, followed by a maintenance course after 1 to 4 weeks. Preferably the maintenance course then consists in an administration of IL-2 at a maintenance dosage, once a week, once every 2 weeks to once a month, during about 1 month, preferably 3 months, still preferably 6 months, or more.

In a particular embodiment, the subject is administered with IL-2 as the single active ingredient effective in treating Sjögren's syndrome.

In another particular embodiment, the subject it administered with IL-2, as well as with other active ingredients, either simultaneously or sequentially. For instance, the subject may be administered with IL-2 in combination with methotrexate, a corticosteroid, and/or with nonsteroidal anti-inflammatory drugs (NSAIDs). However, in preferred embodiments, the dosage of such additional active ingredients can be reduced dramatically, reducing the risk and severity of side effects.

Administration Forms and Routes

Il-2 may be administered using any convenient route, including parenteral, e.g. intradermal, subcutaneous, or intranasal route. The subcutaneous route is preferred. Oral, sublingual or buccal administrations are also encompassed.

IL-2 is typically administered in association (e.g., in solution, suspension, or admixture) with a pharmaceutically acceptable vehicle, carrier or excipient. Suitable excipients include any isotonic solution, saline solution, buffered solution, slow release formulation, etc. Liquid, lyophilized, or spray-dried compositions comprising IL-2 or variants thereof are known in the art and may be prepared as aqueous or nonaqueous solutions or suspensions. Preferably the pharmaceutical compositions comprise appropriate stabilizing agents, buffering agents, bulking agents, or combinations.

The Examples illustrate the invention without limiting its scope.

EXAMPLES

The case reports show that low-dose IL2 can tip the Treg/Teff balance in favor of Tregs and lead to clinical improvement in patients with Sjögren's syndrome.

Patient Selection

Inclusion criteria for study were as follows:
1) documented diagnosis of Sjögren's syndrome (SS) according with ACR criteria (Vitali et al, Classification criteria for Sjögren's syndrome: a revised version of the European criteria proposed by the American-European Consensus Group. Ann Rheum Dis. 2002; 61(6):554-8; Shiboski et al. American College of Rheumatology classification criteria for Sjögren's syndrome: a data-driven, expert consensus approach in the Sjögren's International Collaborative Clinical Alliance cohort. Arthritis Care Res 2012; 64: 475-87);
2) moderately active disease (ESSDAI<5) as described in Seror et al. European League Against Rheumatism Sjögren's Syndrome Disease Activity Index and European League Against Rheumatism Sjögren's Syndrome Patient-Reported Index: a complete picture of primary Sjögren's syndrome patients. Arthritis Care Res, 2013; 65:1358-64; Seror et al, EULAR Sjögren's syndrome disease activity index (ESSDAI): a user guide, RMD Open, 2015, 20; 1(1).

3) under standard treatment (≥2 months) at the time of inclusion.

Exclusion criteria included co-infection with HBV or HIV, several organ damages (heart failure, renal insufficiency, or hepatic insufficiency, or lung failure), pregnancy and drug addiction.

Treatment

Each patient received 1 MUI/day of aldesleukin from Day-1 to Day-5 (the induction period), and then every 2 weeks from Day-15 to Day-180 (the maintenance period). This protocol is referred to as "ldIL-2" (low dose IL-2) therapy.

Patients are thereafter being followed up for 2, 6 and 12 months.

Results

Case reports from the first 3 patients treated are presented below.

Patient 2-12-03-A-S: Diagnostic: Sjögren's syndrome with anti-SSA+, Biermer's disease, Psoriasis, Chronic Urticaria and Hashimoto's thyroiditis; female, 66 years old. Regular treatment: methotrexate 10 mg/week.

Under ldIL-2 therapy, the patient has dramatically decreased arthralgia and asthenia and morning stiffness. In the same time, Anti-SSA antibodies decreased and became undetectable at 6 months ldIL-2 therapy.

2-12-01R-A: Diagnostic: Sjögren's syndrome with anti-SSA+; female, 36 years old. Regular treatment: corticosteroids (10 mg/d) and hydroxychloroquine 400 mg/d.

Under ldIL-2 therapy, the patient has dramatically decreased arthralgia and asthenia and morning stiffness. This clinical benefit was maintained 2.5 months after treatment discontinuation.

1-12-04-C-D: Diagnostic: Sjögren's syndrome with anti-SSA+; female, 63 years old. Regular treatment: methotrexate 10 mg/week and hydroxychloroquine 400 mg/d. Under ldIL-2 therapy, the patient has dramatically decreased arthralgia and asthenia and morning stiffness. This clinical benefit was maintained 2.5 months after treatment discontinuation.

Additional results, including 7 patients, are shown on FIGS. 1-4.

Figure 2:
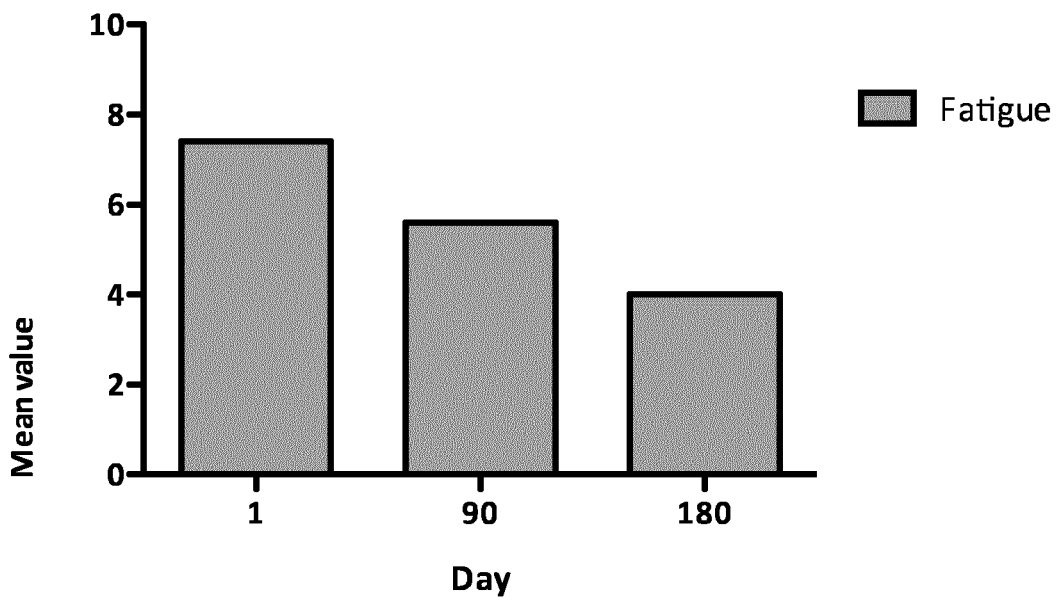
FIG. 2 is a graph that shows alleviation of chronic fatigue in the same 7 subjects with Sjögren's syndrome.

FIGS. 1 and 2 show alleviation of pain (arthralgia) and chronic fatigue, evaluated by physicians at at baseline, month 3 and month 6.

Figure 3:
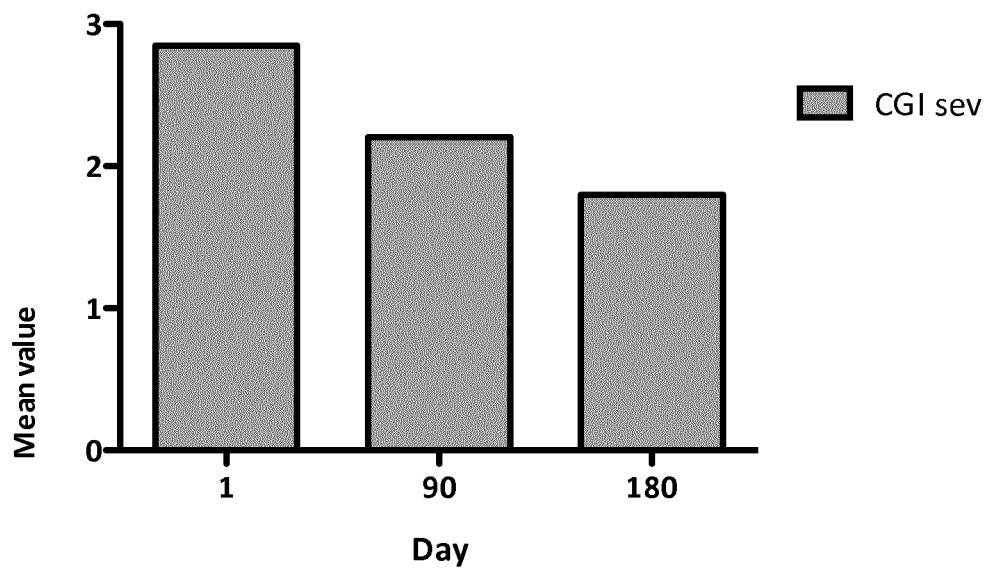
FIG. 3 shows significant improvement of Clinical Global Impression (CGI) severity in the same 7 subjects with Sjögren's syndrome.

FIG. 3 shows significant improvement of Clinical Global Impression (CGI) score. This scale is described in Busner and Targum, Psychiatry Edgmont, 2007, 4:28-37.

Figure 4:
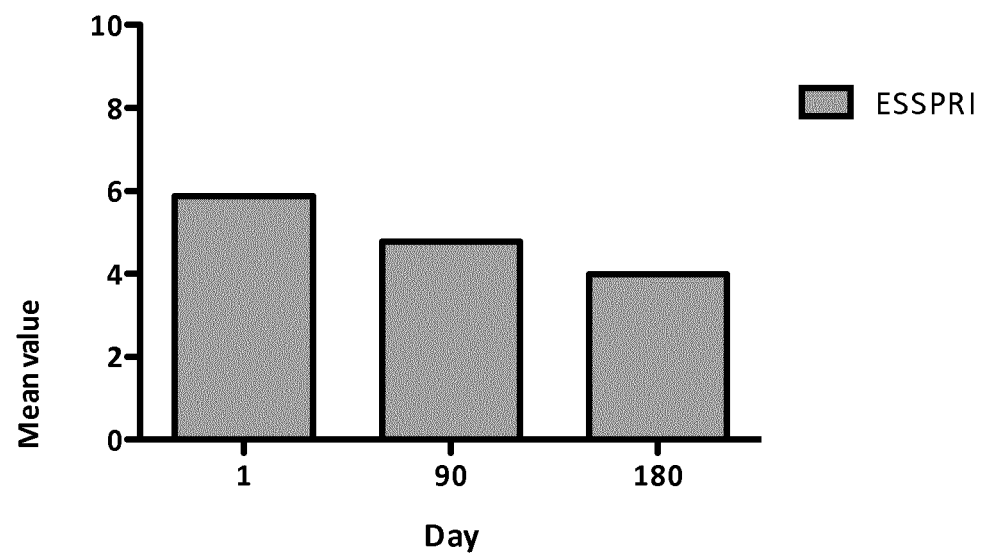
FIG. 4 shows improvement of EULAR Sjögren's Syndrome Patient Reported Index (ESSPRI) in the same 7 subjects with Sjögren's syndrome.

FIG. 4 shows improvement of EULAR Sjogren's Syndrome Patient Reported Index (ESSPRI). This index is described in Seror et al, 2011, Ann Rheum Dis. 70(6):968-72.

The invention claimed is:

1. A method for treating Sjögren's syndrome in a subject in need thereof, wherein the subject is administered with Interleukin-2 (IL-2) at a dose of 3.5 MIU/day or less; and wherein the treatment comprises at least a first course, in which the interleukin-2 is administered to the subject once per day during at least 2 or 3 consecutive days, followed by a maintenance treatment, which consists of an administration of IL-2 once or twice a week, every one or two weeks, or once a month, during a period of at least one month.

2. The method according to claim 1, wherein the IL-2 is administered at a dose of 1-1.5 MIU/day.

3. The method of claim 1, wherein the interleukin-2 is administered by subcutaneous route.

4. The method of claim 1, wherein the treatment reduces the number and/or severity of inflammatory episodes.

5. The method of claim 1, wherein the subject is a human.

6. The method of claim 1, wherein the IL-2 is conjugated to at least one PEG moiety.

7. The method of claim 1, wherein the IL-2 is conjugated to an immunoglobulin, or a Fc region of an immunoglobulin.

8. The method of claim 1, wherein the IL-2 is human IL-2 or an active analogue thereof, which is aldesleukin.

9. The method of claim 8, wherein the IL-2 is human IL-2.

10. The method according to claim 8, wherein the IL-2 is aldesleukin.

11. The method according to claim 1, wherein in the first course, the IL-2 is administered to the subject once per day for 3-7 days.

12. The method according to claim 1, wherein in the first course, the IL-2 is administered to the subject once per day for 4-5 days.

13. The method according to claim 1, wherein the first course is followed by the maintenance treatment after about 1 to about 4 weeks.

14. The method according to claim 1, wherein the maintenance treatment is for about 3 months to about 12 months.

* * * * *

SEQUENCE LISTING

```
<160> NUMBER OF SEQ ID NOS: 2

<210> SEQ ID NO 1
<211> LENGTH: 133
<212> TYPE: PRT
<213> ORGANISM: Homo sapiens

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
            85                  90                  95

Lys Gly Ser Glu Thr Thr Phe Met Cys Glu Tyr Ala Asp Glu Thr Ala
        100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 2
<211> LENGTH: 132
<212> TYPE: PRT
```

```
<213> ORGANISM: Artificial Sequence
<220> FEATURE:
<223> OTHER INFORMATION: aldesleukin

<400> SEQUENCE: 2

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Lys Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
            115                 120                 125

Ser Thr Leu Thr
        130
```